(12) United States Patent
Goer

(10) Patent No.: US 9,656,098 B2
(45) Date of Patent: *May 23, 2017

(54) RADIOTHERAPY COMBINED WITH HYPOXIC CELL SENSITIZERS

(71) Applicant: IntraOp Medical Corporation, Sunnyvale, CA (US)

(72) Inventor: Donald Allen Goer, Sunnyvale, CA (US)

(73) Assignee: INTRAOP MEDICAL CORPORATION, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/952,532

(22) Filed: Nov. 25, 2015

(65) Prior Publication Data

US 2016/0144197 A1 May 26, 2016

Related U.S. Application Data

(63) Continuation of application No. 13/582,409, filed as application No. PCT/US2011/026674 on Mar. 1, 2011.

(60) Provisional application No. 61/309,388, filed on Mar. 1, 2010.

(51) Int. Cl.
*A61N 5/06* (2006.01)
*A61N 5/10* (2006.01)
*A61K 31/4168* (2006.01)
*A61K 41/00* (2006.01)

(52) U.S. Cl.
CPC .......... *A61N 5/062* (2013.01); *A61K 31/4168* (2013.01); *A61K 41/0038* (2013.01); *A61N 5/10* (2013.01); *A61N 5/1001* (2013.01); *A61N 2005/1098* (2013.01)

(58) Field of Classification Search
CPC .............. A61K 41/0038; A61N 5/1027; A61N 5/0601; A61N 5/10; A61N 5/1015
See application file for complete search history.

(56) References Cited

U.S. PATENT DOCUMENTS

| 4,797,397 A * | 1/1989 | Suto ..................... C07D 233/91 514/183 |
| 5,086,068 A | 2/1992 | Raleigh et al. |
| 5,192,784 A | 3/1993 | Bahal et al. |
| 5,321,271 A | 6/1994 | Schonberg et al. |
| 5,418,372 A | 5/1995 | Schonberg et al. |
| 5,778,043 A * | 7/1998 | Cosman ............... A61N 5/1049 378/206 |
| 6,159,443 A * | 12/2000 | Hallahan ............ A61K 51/1203 424/1.17 |
| 6,524,832 B1 | 2/2003 | Kufe et al. |
| 7,070,968 B2 | 7/2006 | Kufe et al. |
| 2002/0198135 A1 | 12/2002 | Dang et al. |
| 2004/0109823 A1* | 6/2004 | Kaplan .................. A61L 31/18 424/1.11 |
| 2004/0260142 A1 | 12/2004 | Lovoi |
| 2005/0259786 A1 | 11/2005 | Fantini et al. |
| 2006/0009468 A1 | 1/2006 | Crooks et al. |
| 2009/0226431 A1* | 9/2009 | Habib ........................ C07J 9/00 424/133.1 |
| 2011/0117078 A1 | 5/2011 | Moussa et al. |
| 2013/0137916 A1 | 5/2013 | Goer |

FOREIGN PATENT DOCUMENTS

| WO | WO-9113633 A1 | 9/1991 |
| WO | WO-0043045 A1 | 7/2000 |
| WO | WO-0066182 A1 | 11/2000 |
| WO | WO-0220500 A2 | 3/2002 |
| WO | WO-2007041546 A2 | 4/2007 |
| WO | WO-2008154927 A1 | 12/2008 |

OTHER PUBLICATIONS

Brown, et al. Stereotactic ablative radiotherapy should be combined with a hypoxic cell radiosensitizer. Int J Radiat Oncol Biol Phys. Oct. 1, 2010;78(2):323-7. doi: 10.1016/j.ijrobp.2010.04.070.
Brown, M. Hypoxic Cell Radiosensitizers: The End of an Era? Regarding Lee et al., IJROBP 32:567-576; 1995. Int. J. Radiation Oncology Biol. Phys., vol. 32, No. 3, pp. 883-885 (1995).
Czito, et al. Chapter 15: IntraOperative Irradiation. Clinical Radiation Oncology, 2d. ed., pp. 315-329, L. Gunderson and J. Tepper, Sr. Editors.
Drzymala, et al. A phase I-B trial of the radiosensitizer: etanidazole (SR-2508) with radiosurgery for the treatment of recurrent previously irradiated primary brain tumors or brain metastases (RTOG Study 95-02). Radiother Oncol. Apr. 2008;87(1):89-92. doi: 10.1016/j.radonc.2008.02.006. Epub Mar. 14, 2008.
Halberg, et al. RTOG #89-06: A Phase I Study to Evaluate Intraoperative Radiation Therapy and the Hypoxic Cell Sensitizer Etanidazole in Locally Advanced Malignancies. Int. J. Radiation Oncology Biol. Phys., vol. 28, No. 1, pp. 201-206 (1994).
International search report and written opinion dated Apr. 18, 2011 for Application No. PCT/US2011/026674.
Karasawa, et al. Efficacy of novel hypoxic cell sensitizer doranidazole in the treatment of locally advanced pancreatic cancer: Long-term results of a placebo-controlled randomized study. Radiotherapy and Oncology, vol. 87, pp. 326-330 (2008).

(Continued)

*Primary Examiner* — Christine H Matthews
*Assistant Examiner* — Joshua D Lannu
(74) *Attorney, Agent, or Firm* — Wilson Sonsini Goodrich & Rosati

(57) ABSTRACT

The invention discloses a method of treating cancer in a patient, comprising administering to the patient a radiation sensitizer selected from nitroimidazoles in an amount effective to sensitize a patient to radiation and subjecting the patient to radiation therapy. In certain embodiments the radiation sensitizer is etanidazole or doranidazole.

10 Claims, No Drawings

(56) References Cited

OTHER PUBLICATIONS

Lee, et al. Results of an RTOG Phase III Trial (RTOG 85-27) Comparing Radiotherapy Plus Etanidazole with Radiotheraphy Alone for Locally Advanced Head and Neck Carcinomas. Int. J. Radiation Oncology Biol. Phys., vol. 32, No. 3, pp. 567-576 (1995).
Marcus, et al. A Phase I Trial of Etanidazole and Hyperfractionated Radiotherapy in Children with Diffuse Brainstem Glioma. Int. J. Radiation Oncology Biol. Phys., vol. 55, No. 5, pp. 1183-1185 (2003).
Notice of allowance dated Apr. 19, 2016 for U.S. Appl. No. 13/582,409.
Office action dated Jan. 7, 2016 for U.S. Appl. No. 13/582,409.
Office action dated Jun. 16, 2015 for U.S. Appl. No. 13/582,409.
Ono, et al. Radiosensitizing effect of misonidazole on mammary carcinoma of C3H mice. Kawasaki Medical Journal 1978 JP, vol. 4, No. 3, 1978, pp. 183-191, ISSN: 0385-0234.
Sasai, et al. Pharmacokinetics of intratumoral RK-28, a new hypoxic radiosensitizer. Inter. J. of Radiation: Oncology Biol. Phys., vol. 24, No. 5, pp. 959-963 (Jan. 1992).
Sunamura, et al. Phase III Trial of Radiosensitizer PR-350 Combined with Intraoperative Radiotherapy for the Treatment of Locally Advanced Pancreatic Cancer. Pancreas, vol. 28, No. 3, pp. 330-334 (Apr. 2004).
Wasserman, TH. A Phase II Trial of the Radiosensitizer: Etanidazole (SR-2508) with Radiosurgery for the Treatment of Recurrent Previously Irradiated Primary Brain Tumors or Brain Metastases (RTOG Protocol #95-02). Int. J. Radiation Oncology Biol. Phys., vol. 45, No. 3 Supp., p. 272 (1999).
Willett, et al. IORT—Current and Future Status—2002. Astro Refresher Course, pp. 1-24 (Oct. 2002).

\* cited by examiner

RADIOTHERAPY COMBINED WITH HYPOXIC CELL SENSITIZERS

CROSS REFERENCE TO RELATED APPLICATIONS

This application is a Continuation Application which claims the benefit of U.S. application Ser. No. 13/582,409, filed Feb. 13, 2013; which is a national stage application of PCT/US11/26674, filed Mar. 1, 2011, which claims the benefit under 35 U.S.C. §119(e) of U.S. Provisional Application No. 61/309,388, filed on Mar. 1, 2010, each disclosure of which is incorporated herein by reference in its entirety.

BACKGROUND OF THE INVENTION

Cancer is one of the deadliest illnesses in the United States. It accounts for nearly 600,000 deaths annually, and costs billions of dollars for those who suffer from the disease. This disease is in fact a diverse group of disorders, which can originate in almost any tissue of the body. In addition, cancers may be generated by multiple mechanisms including pathogenic infections, mutations, and environmental insults (see, e.g., Pratt et al., *Hum. Pathol.* 36:861-70, 2005). Current cancer treatments include, among others, surgery, chemotherapeutics, radiation therapy, immunotherapy, and photodynamic therapy. However, none of these treatments is completely effective, and each has its own associated side effects.

Hypoxia is a characteristic feature of many tumors, particularly locally advanced and recurrent solid cancers resulting from an imbalance between oxygen supply and consumption (see Vaupel et al., *Oncologist* 9 Suppl. 5:4-9, 2004). Cancer tumor hypoxia can reduce the effectiveness of radiotherapy, some oxygen-dependent cytotoxic agents, and photodynamic therapy. The presence of hypoxia has been demonstrated in a wide variety of human cancers, including colorectal, cervix, breast, lung, brain, pancreas, head and neck, and prostate. Many of these tumors contained regions of severe hypoxia (<5 mmHg oxygen). Clinically, the duration of disease and progression free survival correlates inversely with the degree of tumor hypoxia. For example, in patients with squamous carcinoma of the head and neck, the one-year disease-free survival was 78% for patients with median tumor $pO_2$>10 mm Hg but only 22% for median $pO_2$<10 mm (Brizel, et al., Int. J. Radiat. Oncol. Biol. Phys. 38:285-9, 1997). Hypoxic cells exhibit increased resistance to standard radiation and chemotherapy treatment programs, as these cells are relatively isolated from the blood supply and because radiation and chemotherapy preferentially kill rapidly dividing cell populations.

Pharmaceutical compounds which sensitize hypoxic cells to radiation therapy have shown promising results. However, there remain drawbacks to the safety and efficacy in the current methods.

SUMMARY OF THE INVENTION

The invention comprises a method of treating cancer in a patient, comprising administering to the patient a radiation sensitizer selected from nitroimidazoles in an amount effective to sensitize a patient to radiation; and subjecting the patient to radiation therapy. In certain embodiments the radiation sensitizer is etanidazole or doranidazole.

In certain embodiments, the radiation therapy is intraoperative radiation therapy ("IORT"). In particular embodiments, the radiation is localized to a tumor site. The patient may be subjected to intraoperative radiation prior to resection of the tumor or following resection of the tumor. The tumor site may comprise different types of cells including cancerous and benign cells. In certain embodiments, the radiation therapy is stereotactic body radiotherapy ("SBRT") or stereotactic radiosurgery ("SRS").

The radiation may be ionizing radiation such as particle beam radiation. The particle beam radiation may be selected from any of electrons, protons, neutrons, heavy ions such as carbon ions, or pions. The ionizing radiation may be selected from x-rays, UV-light, γ-rays, or microwaves. In certain embodiments, the radiation therapy may comprise subjecting the patient to one or more types of radiation therapy.

In certain embodiments, the method of the invention comprises administering radiation with a mobile electron beam therapy system. The radiation may be delivered before, during or after a surgical procedure. In certain embodiments, the patient is administered a radiation sensitizer and subjected to radiation therapy within a short time thereafter, such as within about 2 hours of each other, such as within about 1 hour of each other, e.g., within about 40 minutes of each other.

In certain embodiments, the method of the invention is for the treatment of cancer selected from colorectal cancer, stomach cancer, brain cancer, lung cancer, pancreatic cancer, prostate cancer, cancer of the head or neck, breast cancer, or cancer of the oral cavity. In particular embodiments the cancer is lung or colorectal. In certain embodiments, the method for treating cancer comprises: (a) administering to the patient a pharmaceutically acceptable preparation which includes a therapeutically effective amount of a radiation sensitizer selected from etanidazole and doranidazole; and (b) subjecting the patient to a therapeutically effective amount of radiation.

In certain embodiments, the method for treating cancer comprises: (a) administering to the patient a radiation sensitizer selected from etanidazole and doranidazole in an amount effective to sensitize the patient, e.g., the tumor, tumor bed and surrounding tissue, to ionizing radiation; and (b) subjecting the patient to intraoperative radiation.

In certain embodiments, the method comprises (a) administering to the patient a pharmaceutically acceptable composition comprising a therapeutically effective amount of a radiation sensitizer; (b) performing resection of a tumor; and (c) subjecting the patient's body cavity at the site of the resection of step (b) with a therapeutically effective amount of intraoperative radiation therapy.

In certain aspects, the radiation sensitizer of the invention is associated with a targeting moiety. The targeting moiety may be selected from an antibody such as an antibody which targets a tumor-specific antigen. The targeting moiety may be covalently associated with the radiation sensitizer or the targeting moiety may be non-covalently associated with a radiation sensitizer. The radiation sensitizer and targeting moiety may be associated within a liposome.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Overview

Work has been going on for many years on methods for increasing the radiosensitivity of tumors relative to that of normal tissues. One of these methods involves administering a pharmaceutical that sensitizes the tumor cells to radiation. The use of such pharmaceuticals, called radiosensitizers, provides a method of increasing the radiosensitivity of tumors to radiation therapy, avoiding the need to increase radiation dosages to levels that are harmful to surrounding organs and tissues.

The largest class of radiosensitizers is the hypoxic cell sensitizers. These pharmaceuticals overcome the radioresistance afforded some tumor cells by their lack of oxygen, i.e., hypoxia. Most tumors exhibit some degree of hypoxia, with locally advanced and recurrent tumors exhibiting especially high levels of hypoxia. The decreased oxygenation of tumor cells is a consequence of the structural and functional disturbances to the tumor vasculature that inhibit the normal delivery of oxygen. Within this class, electron-affinic nitroimidazoles have been found in general to radiosensitize hypoxic tumor cells. Two nitroimidazoles, misonidazole and metronidazole, have been used clinically; however, clinical applications are limited by neurotoxicity and lower dosages are ineffective at sensitizing tumor cells to traditional external beam radiation therapy.

Etanidazole, an electron-affinic 2-nitroimidazole, displays a sensitizing ability similar to misonidazole but has less lipophilicity and thus less neurotoxicity, allowing higher doses. Studies of the maximum tolerated dose of etanidazole have shown that 12 $gm/m^2$ may safely be given to patients who receive single dose administrations. Above this level, the incidence of side effects increases in patients who have received single dose administrations of etanidazole. Thus, methods of exploiting the reduced neurotoxicity of etanidazole for killing hypoxic cells would be advantageous.

In traditional external beam radiation therapy coupled with radiosensitizer administration, a beam of high energy X-rays, generated outside the patient by a linear accelerator, is delivered to a tumor. Most body tissue does not absorb or block X-rays, so they progress through the body, constantly releasing energy. When the cancer tumor is within the path of the X-ray, it receives some of that radiation; however, surrounding healthy tissue receives radiation as well. In order to limit the extent of collateral tissue damage, oncologists typically bombard the tumor area with the lowest level of effective radiation from many different points of entrance in an attempt to minimize damage to normal tissues. Even modern external beam radiation systems with improved real-time imaging of the patient anatomy will inevitably treat substantial normal tissue volumes when targeting the tumor.

Other energy sources, such as particle beams contain charged atomic particles. Particle beams have tremendous energy but also high mass and as such they slow down as they encounter body tissue. Particles can be controlled, for example, to release their energy at a specific point in the body. Particle beam therapy uses electrons, neutrons, heavy ions (such as protons, carbon ions and helium); and pi-mesons (also called pions).

Recent approaches to radiotherapy use high-dose radiation with precise focus on the cancerous area, limiting exposure of healthy cells to radiation. Stereotactic Body Radiation Therapy ("SBRT"), uses image-guided, focused high-dose external beam x-ray radiation to irradiate a tumor, often in a single fraction. To avoid the excessive toxicity which can occur to normal tissue, however, many tumors, even when targeted with SBRT, must be irradiated over two to five fractions, each fraction of lower dose than single fraction SBRT. The reduced dose per SBRT fraction may not be adequate to destroy the hypoxic component of the tumor.

Stereotactic radiosurgery ("SRS"), is a non-surgical procedure that delivers a single high-dose of precisely-targeted radiation typically targeted to the brain, head and neck using highly focused gamma-ray or x-ray beams that converge on the specific area or areas where the tumor resides, minimizing the amount of radiation to healthy tissue. Although stereotactic radiosurgery is often completed in a one-day session, physicians sometimes recommend multiple treatments, especially for tumors larger than one inch in diameter. The procedure is usually referred to as fractionated stereotactic radiosurgery when two to five treatments are given and as stereotactic radiotherapy when more than five treatments are given.

Intraoperative Radiation Therapy ("IORT") is the delivery of radiation at the time of surgery using a focused high-dose radiation directed to the site of the cancerous cells. TORT is characterized by a concentrated beam of ionizing radiation to cancerous tumors while the patient is exposed during surgery, i.e., radiation is delivered within an open body cavity. IORT has an advantage of being able to temporarily displace healthy tissue from the path of the radiation beam so as to reduce the exposure of normal tissues to the radiation and contact the tumor site more directly. Single dose IORT in excess of 8-10 Gy, is effective at destroying tumor stem cells and its host-derived microvascular structure, thereby inhibiting DNA repair in the tumor, but hypoxic cells within the tumor may require doses in excess of 20-24 Gy, doses that could exceed normal tissue tolerance.

The present invention relates to methods of treating cancer in a patient comprising administering to the patient a radiation sensitizer such as a hypoxic cell sensitizer and subjecting the patient to radiation therapy. In certain embodiments of the invention, coupling a radiation sensitizer with radiation techniques that employ focused high-dose radiation therapy increases the exposure of tumor cells to radiation while protecting the surrounding tissues and organs. The radiation sensitizer may be administered prior to the administration of this focused high-dose radiation therapy, and due to the high local intensity of the radiation, the surrounding tissues and organs are spared the damage of non-directed radiation therapy. In one embodiment of the invention, a patient is administered a radiation sensitizer and then subjected to IORT. In another embodiment, administration of a radiation sensitizer is followed by SBRT or SRS. Such treatment may be used to treat any solid cancerous tumor, particularly tumors that are resistant to traditional therapies, such as locally advanced and recurrent head and neck tumors and recurrent rectal cancer.

In certain embodiments, the radiation sensitizer is a nitroimidazole, such as a 2-nitroimidazole, e.g., etanidazole or doranidazole. In certain embodiments, the radiation sensitizer is administered to a patient prior to or during a surgical procedure to remove a tumor. In such embodiments, the patient undergoes a surgical procedure to remove a tumor and during the surgery, the patient is subjected to IORT such as during or after the resection of the tumor. In certain embodiments, the patient is subjected to intraoperative radiation more than once during the surgical procedure such as before the resection of the tumor and following the tumor removal. In another embodiment, administration of a nitroimidazole is followed by SBRT or SRS. The patient may be administered the radiation sensitizer within 2 hours prior to being subjected to radiation therapy, such as within 1 hour or within 40 minutes.

Definitions

As used herein the specification, "a" or "an" may mean one or more. As used herein in the claim(s), when used in conjunction with the word "comprising", the words "a" or "an" may mean one or more than one. As used herein "another" may mean at least a second or more.

As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can benefit from a combined effect of different therapeutic compounds.

As used herein "fraction" or "fractionation" of radiation therapy is dividing the total dose of radiation therapy into several smaller doses delivered over a period of time. The total dosage may be fractionated to allow normal cells time to recover, to allow tumor cells that were in a relatively radio-resistant phase of the cell cycle during one treatment to cycle into a sensitive phase of the cycle before the next fraction is given, or to allow hypoxic tumor cells to reoxygenate between fractions, improving the tumor cell kill. The summed value of individual fractionized dose should add up to about the total dose of radiation therapy prescribed.

The term "preventing" is art-recognized, and when used in relation to a condition, such as a local recurrence (e.g., pain), a disease such as cancer, a syndrome complex such as heart failure or any other medical condition, is well understood in the art, and includes prophylactic administration of a composition which reduces the frequency of, decreases the severity of, or delays the onset of symptoms of a medical condition in a subject relative to a subject which did not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

In the present invention, the term "radiation sensitizer" or "radiosensitizer" means a compound which enhances the effect of radiation.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

As used herein, the term "surgery" is a medical technology consisting of a physical intervention on tissues. A procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. Surgery can last from minutes to hours, but is typically not an ongoing or periodic type of treatment. As used herein, "before surgery" refers to the period of time prior to the physical intervention on tissues, wherein intervention of tissues refers to cutting of a patient's tissues. Treatments administered before surgery may be administered in exemplary embodiments about 2 hours before, about 1 hour before, about 45 minutes before, about 30 minutes before, about 20 minutes before or about 10 minutes before the physical intervention on tissues. As used herein, "during surgery" refers to the period of time after which the surgical procedure has commenced, i.e., the physical intervention of tissues and continues until the time that the task being performed within the tissue is complete. For example, in the case where a cancer patient is subjected to resection of a cancerous tumor, tissue is incised revealing the tumor, the tumor is removed during the surgical procedure, radiation may be administered to the patient and then the tissue is sutured, marking the completion of the surgery. Such radiation would be considered to have been delivered during the surgery. The completion of the surgical procedure is often marked by the closure of tissue through suturing or stapling.

Exemplary Embodiments

In certain embodiments, the invention provides a method of treating cancer in a patient, comprising administering to the patient a radiation sensitizer selected from nitroimidazoles in an amount effective to sensitize a patient to radiation and subjecting the patient to radiation therapy. Nitroimidazoles of the invention may be selected from any compound with the characteristic features of a nitroimidazole functionality and which function as radiation sensitizers, such as hypoxic cell sensitizers. Exemplary nitroimidazoles of the invention include etanidazole, doranidazole, metronidazole, misonidazole, tinidazole, nimorazole and compounds disclosed in U.S. Pat. No. 4,282,232. In particular embodiments, the nitroimidazole is selected from a 2-nitroimidazole such as etanidazole or doranidazole.

The methods of the invention may be used to treat any cancer, including but not limited, to a solid tumor, such as brain, lung, liver, spleen, kidney, lymph node, small intestine, pancreas, blood cells, bone, colon, rectum, stomach, breast, endometrium, prostate, testicle, ovary, central nervous system, head, neck, or esophageal cancer. In certain embodiments, the methods of the invention are used to treat rectal cancer, lung cancer or cancer of the head and neck. In particular embodiments, the methods are used to treat rectal cancer. In particular embodiments, the methods are used to treat lung cancer.

In certain aspects the radiation therapy used to treat the patient is intraoperative radiation therapy (IORT). For example, the patient may receive a nitroimidazole radiation sensitizer and IORT while the patient is exposed during surgery, i.e., radiation is delivered within an open body cavity. IORT may be delivered in a single dosage or fractionated in two or multiple doses, e.g., in the duration of a surgical procedure. For example, the patient may be administered etanidazole or doranidazole and subjected to IORT, e.g., within about 1 hour of each other, such as within about 40 minutes of each other. In particular embodiments, a patient suffering from rectal cancer is administered etanidazole and subjected to IORT to treat the rectal cancer, e.g., within about 1 hour of each other.

For patients subjected to IORT, IORT may be administered at one or more stages during a surgical procedure. For example, the patient may be administered a radiation sensitizer and surgically incised to reveal a tumor, at which point radiation is administered directly to the tumor or a portion thereof. The radiation source may be placed in close proximity or in contact with the cancerous tissues or organs. Radiation may be delivered to the patient with a mobile electron beam therapy system.

In certain embodiments, radiation therapy is localized to a tumor site. A patient may be subjected to radiation, e.g., IORT, prior to resection of cancerous cells, e.g., a malignant tumor, such as about 1 hour prior, such as about 40 minutes prior to resection. Alternatively, the patient may be subjected to radiation therapy following resection of cancerous cells, such as within about 1 hour of radiation therapy, or may even be subjected to radiation both prior to and following resection of cancerous cells. In certain exemplary embodiments, the patient undergoes surgical resection of a tumor and radiation therapy is administered to the patient during the surgical procedure, following removal of the tumor, or both during the surgical procedure and following the removal of the tumor. Thus, the method may comprise treating a tumor site with radiation, e.g., during a surgical procedure, after partial resection of the tumor. It would be well in the realm of knowledge of one of skill in the art as to which of the tissues remaining after resection should be treated with radiation therapy. In certain embodiments, the patient is contacted with one or more of IORT, SBRT or SRS at a tumor site.

Radiation localized to a tumor site may contact cancerous or non-cancerous cells. In certain embodiments, the radiation localized to the tumor site may contact non-cancerous cells, i.e., benign cells. For example, the method may comprise treating non-cancerous cells surrounding a tumor site with radiation in order to prevent recurrence of the cancer, e.g., through the irradiation of any microscopic disease that might extend into the normal tissue structures.

In certain embodiments, the surgical procedure is performed in close proximity to the radiation source such that the patient does not need to be moved during, before, or after the surgery to receive IORT. For example, the radiation source may be located in the operating room, e.g., to facilitate access to the radiation source during surgery. In certain embodiments, the radiation is administered at one or more times during a surgical procedure.

A "surgical procedure" or "surgery" referred to in IORT includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may also be used in conjunction with removal of superficial cancers, precancers, or incidental amounts of normal tissue.

In certain embodiments, the radiation delivered with IORT is ionizing. Ionizing radiation may be particle beam radiation, also known as charged particle radiation, which uses beams of charged particles such as electrons, protons (e.g., proton beam radiation), neutrons, pions, or carbon ions. Ionizing radiation may also be selected from x-rays, UV-light, γ-rays or microwaves.

A combination of stereotactic radiation and a radiosensitizer may be used to sensitize the tumor cells and provide highly-focused doses of radiation on the cells. In certain aspects, stereotactic radiation such as SBRT or SRS is used in combination with a nitroimidazole radiation sensitizer, such as a 2-nitroimidazole, to treat cancer. In particular embodiments, the patient is administered a nitroimidazole radiation sensitizer, such as a 2-nitroimidazole, and subjected to SBRT, e.g., within about 1 hour such as within about 40 minutes of each other. In certain embodiments, the patient is administered a nitroimidazole radiation sensitizer, such as a 2-nitroimidazole, and subjected to SRS, e.g., within about 1 hour such as within about 40 minutes of each other. In some embodiments, SBRT or SRS is delivered in a single dose or is fractionated in two or multiple doses such as over a period of hours, days or weeks. In other embodiments, SBRT or SRS is delivered from 2 or more angles of exposure to intersect at the tumor, providing a larger absorbed dose there than in the surrounding, healthy tissue. In still other embodiments, SBRT or SRS is used with etanidazole or doranidazole to treat cancer. In more particular embodiments, a patient suffering from lung cancer is administered etanidazole and subjected to SBRT such as within about 1 hour of each other.

The timing may be varied between the administration of a radiation sensitizer and radiation therapy. In certain aspects, the patient is administered a radiation sensitizer and subjected to radiation therapy, e.g., IORT, SRS or SBRT, within about 2 hours of each other, such as within 1 hour, such as within 40 minutes, preferably such that the organ or tissue to be irradiated has had adequate time to absorb a sufficient concentration of the sensitizer prior to radiation treatment. Thus, the sensitizer may be administered less than 2 hours before radiation treatment, or less than 1 hour such as about 80 minutes, about 70 minutes, about 60 minutes, about 50 minutes, about 40 minutes, about 30 minutes, about 20 minutes or about 10 minutes before radiation treatment.

A radiation sensitizer, such as a 2-nitroimidazole, may be administered to a patient before each fractionated dose of radiation is delivered, for example, within about 1 hour of each fractionated dose of radiation. In certain embodiments, the patient is administered etanidazole with about 1 hour, for example, within about 40 minutes of each fractionized dose of radiation therapy, such as SRS or SBRT.

A radiation sensitizer, such as 2-nitroimidazole, may be administered to a patient before each single dose of radiation is delivered, for example, within about 1 hour of each single dose of radiation. For example, a patient may receive a single dose of IORT radiation during a surgical resection and a single dose of SBRT a day or more after the surgery, both radiation doses of which may be preceded by administration of a radiation sensitizer such as a 2-nitroimidazole. Each single dose may be targeted to the same tumor site or different tumor sites. In certain embodiments, two or more single radiation doses are targeted to the same tumor site.

SBRT or SRS may be administered independently of other surgical procedures. In certain embodiments, the patient receives a single dose or fractionated doses of SBRT or SRS without undergoing any surgery. Patients may also receive one or more doses of SBRT or SRS, which may be preceded by administration of a radiation sensitizer, such as 2-nitroimidazole within, e.g., about 1 hour, of the one or more doses of SBRT or SRS.

Radiation may be selected from any type suitable for treating cancer. Radiation may come from a machine outside the body (external radiation), may be placed inside the body (internal radiation), or may use unsealed radioactive materials that go throughout the body (systemic radiation therapy). The type of radiation to be given depends on the type of cancer, its location, how far into the body the radiation will need to penetrate, the patient's general health and medical history, whether the patient will have other types of cancer treatment, and other factors. In certain embodiments, radiation is delivered in more than one manner, e.g., internal radiation and external radiation.

One or more forms of radiation may be coupled with the radiation sensitizer of the invention. In certain embodiments, the patient is administered a radiation sensitizer and subjected to a form of external radiation and one or more additional forms of radiation. External radiation may be intraoperative electron beam radiation therapy, which may, for example, be administered during a surgical procedure, as discussed above. In particular embodiments, the patient is subjected to TORT and a second type of radiation selected from external, internal and systemic radiation. In certain particular embodiments, the patient is subjected to intraoperative radiation therapy and external beam radiation therapy.

In those embodiments where the patient is subjected to more than one form of radiation therapy, the patient may be subjected to two or more forms of radiation therapy at the same time, in sequence, in fractional doses at the same time or in fractional doses sequentially, in fractional doses alternating, and/or any combination thereof. In certain embodiments, intraoperative radiation therapy is administered before, during and/or after a surgical procedure and a second form or radiation therapy is administered at a later time such as hours after the surgical procedure, and/or days after the surgical procedure, and/or weeks after the surgical procedure. In certain embodiments, the patient is treated with radiation therapy leading up to the surgical procedure such as hours before the surgical procedure, days before the surgical procedure and/or weeks before the surgical procedure.

Radiotherapy of the invention may comprise a cumulative external irradiation of a patient in a dose of 1 to 100 Gy. A preferred range of the irradiation dose is 1 to 60 Gy. In certain embodiments, the dose of radiation therapy is less than 90 Gy, such as less than 80 Gy, such as less than 70 Gy, such as less than 60 Gy, such as less than 50 Gy, such as less than 40 Gy, such as less than 30 Gy, such as less than 20 Gy. In certain embodiments the dose or radiation therapy is between about 10 to 100 Gy, such as from about 20 to 80 Gy, such as about 30 to 70 Gy, such as about 40 to 60 Gy. In certain embodiments, the irradiation dose is selected from 5-25 Gy, such as from 10-20 Gy.

An external irradiation dose may be administered in 1 to 60 fractional doses, such as from 5 to 30 fractional doses. In certain embodiments, the fractionized doses are administered with about 1.5 to about 2 Gy per fraction, such as about 1.5 Gy, such as about 1.6 Gy, such as about 1.7 Gy, such as about 1.8 Gy, such as about 1.9 Gy, such as about 2.0 Gy, such as about 2.1 Gy, such as about 2.2 Gy, such as about 2.3 Gy such as about 2.4 Gy, such as about 2.5 Gy per fractionized dose.

Fractionated doses of radiation therapy may be administered at intervals. In certain embodiments, the fractionized doses are administered over a period of minutes, hours, or weeks such as 1 to 26 weeks, such as from about 1 to 15 weeks, such as from 2 to 12 weeks. In certain embodiments, the fractionized doses are administered over a period less than about 15 weeks, such as less than about 14 weeks such as less than about 13 weeks, such as less than about 12 weeks, such as less than about 11 weeks, such as about less than about 10 weeks, such as less than about 9 weeks, such as less than about 8 weeks, such as less than about 7 weeks, such as less than about 6 weeks, such as less than about 5 weeks, such as less than about 4 weeks. In certain embodiments, the cumulative external irradiation is a therapeutically effective amount of radiation for killing cells.

In other embodiments, the radiation therapy is administered in a single dosage rather than in fractionized doses. For example, the single dose may be administered with about 1-30 Gy per dose, such as from 5-20 Gy or such as about 10-15 Gy. IORT may be administered with a dose of about 5-20 Gy. In certain embodiments, a radiation sensitizer is administered to a patient and the patient is subjected to a single dose of radiation therapy within 10 minutes, within 20 minutes, within 30 minutes, within 40 minutes, within 50 minutes or within an hour of the administration of the sensitizer.

In some embodiments, the invention provides methods of administering reduced dosages of radiation by combining intraoperative radiation with radiation sensitizers of the invention. Brown et al. (*Int. J. Radiation Oncology Biol. Phys.*, 2010, 78 (1): 323-327) provide modeling data in favor of using the radiosensitizer etanidazole (ET) in combination with stereotactic ablative radiotherapy (SABR). By calculating the expected level of tumor cell killing following SABR, Brown et al. indicate that administration of ET prior to SABR will reduce the dose and frequency of irradiation required to treat tumors and metastases, particularly in tumors with high levels of hypoxia. Thus, in particular embodiments, the radiation is reduced by up to 1%, up to 5%, up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, and up to 99% as compared to intraoperative radiation therapy delivered without sensitizers. Moreover, the dosage of radiation in intraoperative radiation therapy may reduce by 25-50% relative to the amount of external beam radiation therapy that may be required to treat the disease without the sensitizer. Accordingly, the invention also provides a method of administering reduced dosages of radiation to a patient by combining IORT, SBRT or SRS with a radiation sensitizer selected from nitroimidazoles, wherein the radiation is reduced by up to 75% relative to radiation therapy delivered without sensitizers.

The energy source used for the radiation therapy may be selected from X-rays or gamma rays, which are both forms of electromagnetic radiation. X-rays are created by machines called linear accelerators. Depending on the amount of energy the x-rays have, they can be used to destroy cancer cells on the surface of the body, i.e., lower energy, or deeper into tissues and organs, i.e., higher energy. Compared with other types of radiation, x-rays can deliver radiation to a relatively large area. Gamma rays are produced when isotopes of certain elements, such as iridium and cobalt 60, release radiation energy as they decay. Each element decays at a specific rate and each gives off a different amount of energy, which affects how deeply it can penetrate into the body. Gamma rays produced by the decay of cobalt 60 are used in the treatment called the "gamma knife."

The energy source for the radiation therapy may be selected from particle beams, which use fast-moving subatomic particles instead of photons. This type of radiation may be referred to as particle beam radiation therapy or particulate radiation. Particle beams may be created by linear accelerators, synchrotrons, betatrons and cyclotrons, which produce and accelerate the particles required for this type of radiation therapy. Particle beam therapy may use electrons, which are produced by an x-ray tube, this may be called electron-beam radiation; neutrons, which are produced by radioactive elements and special equipment; heavy ions such as protons, carbon ions and helium; and pi-mesons, also called pions, which are small, negatively charged particles produced by an accelerator and a system of magnets. Unlike x-rays and gamma rays, some particle beams, depending on the energy, can penetrate only a short distance into tissue. Therefore, they are often used to treat cancers located on the surface of or just below the skin.

In the present invention, the term "ionizing radiation" means radiation comprising particles or photons that have sufficient energy or can produce sufficient energy via nuclear interactions to produce ionization, i.e., gain or loss of electrons. The amount of ionizing radiation needed to kill a given cell generally depends on the nature of that cell. Means for determining an effective amount of radiation are well known in the art. Used herein, the term "an effective dose" of ionizing radiation means a dose of ionizing radiation that produces an increase in cell damage or death when given in conjunction with the nitroimidazoles of the invention.

In certain embodiments, the radiation therapy comprises ionizing radiation, particularly electron beam radiation. An electron beam may be delivered intraoperatively to the tumor site using an electron beam therapy system such as the one described in U.S. Pat. Nos. 5,418,372 and 5,321,271 the full disclosure of which is incorporated herein by reference. In particular embodiments, the electron beam therapy system of the invention provides adequate shielding to healthy tissue for primary x-rays generated by the system as well as for scatter radiation.

In particular embodiments, the particle beam therapy is proton beam therapy. Protons deposit their energy over a very small volume, which is called the Bragg peak. The Bragg peak can be used to target high doses of proton beam therapy to a tumor while doing less damage to normal tissues in front of and behind the tumor. Proton beam therapy is generally reserved for cancers that are difficult or dangerous to treat with surgery, such as a chondrosarcoma at the base of the skull, or it is combined with other types of radiation. Proton beam therapy is also being used in clinical trials for intraocular melanoma, i.e., melanoma that begins in the eye, retinoblastoma, i.e., an eye cancer that most often occurs in children under age 5, rhabdomyosarcoma, i.e., a tumor of the muscle tissue, some cancers of the head and neck, and cancers of the prostate, brain, and lung.

In some embodiments, the radiation therapy is stereotactic (or stereotaxic) radiosurgery which uses a large dose of radiation to destroy tumor tissue. In certain exemplary embodiments, where the cancer is in the brain, the patient's head can be placed in a special frame, which is attached or is fitted to the patient's skull. The frame is used to aim high-dose radiation beams directly at the tumor inside the patient's head. The dose and area receiving the radiation are coordinated very precisely resulting in little damage to nearby tissues. In some stereotactic applications, a head frame is not needed. In certain embodiments, real-time imaging systems are used in conjunction with the movement of the accelerator, allowing computer adjustments of the accelerator trajectory to compensate for any motion of the patient's head.

Stereotactic radiosurgery may be done in a variety of ways. One suitable technique uses a linear accelerator to administer high-energy photon radiation to the tumor, i.e., linac-based stereotactic radiosurgery. In another technique, a gamma knife uses cobalt 60 to deliver radiation. In a third technique, heavy charged particle beams such as protons and helium ions are used to deliver stereotactic radiation to the tumor.

In certain embodiments, stereotactic radiosurgery is used in the treatment of small benign and malignant tumors such as brain tumors, e.g., meningiomas, acoustic neuromas, and pituitary cancer. In addition, stereotactic radiosurgery can be used to treat metastatic brain tumors, i.e., cancer that has spread to the brain from another part of the body either alone or along with whole-brain radiation therapy. Whole-brain radiation therapy is a form of external radiation therapy that treats the entire brain with radiation.

Radiation therapy may be stereotactic body radiotherapy, or SBRT. Stereotactic radiotherapy uses essentially the same approach as stereotactic radiosurgery to deliver radiation to the target tissue; however, stereotactic radiotherapy generally uses multiple small fractions of radiation as opposed to one large dose, but certain applications of SBRT may still be accomplished with a single fraction. Stereotactic body radiotherapy may be used to treat tumors in the brain, lung, liver, pancreas, prostate, spine, as well as other parts of the body.

When a source of radiation therapy is internal, the energy used in internal radiation may come from a variety of sources. For example, the radioactive isotope may be radioactive iodine, e.g., iodine 125 or iodine 131, strontium 89, phosphorous, palladium, cesium, iridium, phosphate, cobalt, or any other isotope known in the art. In certain embodiments, the internal radiation is administered as brachytherapy, a radiation treatment based on implanted radioactive seeds emitting radiation from each seed.

Radiation may be delivered directly to the cancer through the use of radiolabeled antibodies, i.e., radioimmunotherapy. Antibodies are highly specific proteins that are made by the body in response to the presence of antigens, i.e., substances recognized as foreign by the immune system. Some tumor cells contain specific antigens that trigger the production of tumor-specific antibodies. Large quantities of these antibodies can be made in the laboratory and attached to radioactive substances, a process known as radiolabeling. Once injected into the body, the antibodies seek out cancer cells, which are destroyed by the radiation. This approach can reduce or minimize the risk of radiation damage to healthy cells. In certain embodiments, the radioimmunotherapy treatments are selected from ibritumomab tiuxetan (Zevalin®) and tositumomab and iodine 131 tositumomab (Bexxar®). Radioimmunotherapy may be used in the treatment of advanced adult non-Hodgkin lymphoma (NHL). In certain embodiments, immunotherapy is used in the treatment of cancers including leukemia, NHL, colorectal cancer, and cancers of the liver, lung, brain, prostate, thyroid, breast, ovary, and pancreas.

In certain aspects, the invention comprises the methods for planning external radiation therapy in order to target the cancerous cells and limit exposure to healthy cells. In certain embodiments, the planning of radiation treatments is performed in two dimensions (width and height) or three dimensions, for example, with three-dimensional (3-D) conformal radiation therapy. In certain embodiments, 3-D conformal radiation therapy uses computer technology to allow doctors to more precisely target a tumor with radiation beams (using width, height, and depth). A 3-D image of a tumor can be obtained using computed tomography (CT), magnetic resonance imaging (MRI), positron emission tomography (PET), or single photon emission computed tomography (SPECT). Using information from the image, special computer programs may design radiation beams that "conform" to the shape of the tumor. In certain embodiments, because the healthy tissue surrounding the tumor is largely spared by this technique, higher doses of radiation can be used to treat the cancer. Improved outcomes with less toxicity with 3-D conformal radiation therapy may be possible for nasopharyngeal, prostate, lung, liver, and brain cancers.

In certain particular embodiments, the radiation therapy is intensity-modulated radiation therapy (IMRT). IMRT is a type of 3-D conformal radiation therapy that uses radiation beams, e.g., x-rays of varying intensities to deliver different doses of radiation to small areas of tissue at the same time. The technology allows for the delivery of higher doses of radiation within the tumor and lower doses to nearby healthy tissue. Some techniques deliver a higher dose of radiation to the patient each day, potentially shortening the overall treatment time and improving the success of the treatment. IMRT may also lead to fewer side effects during treatment. In particular embodiments, the radiation is delivered by a linear accelerator that is equipped with a multileaf collimator (a collimator helps to shape or sculpt the beams of radiation). The equipment can be rotated around the patient so that radiation beams can be sent from the best angles. The beams conform as closely as possible to the shape of the tumor. In certain embodiments, this technology is used to treat tumors in the brain, head and neck, nasopharynx, breast, liver, lung, prostate, and uterus.

Radiation therapy may be used in conjunction with hyperthermia, i.e., the use of heat. In certain embodiments, the combination of heat and radiation can increase the response rate of some tumors.

A radiosensitizer may be administered in conjunction with an additional agent. For example, a nitroimidazole may be administered in conjunction with an additional agent such as a targeting agent, a chemotherapeutic agent or a second radiosensitizer. Targeting agents include any suitable agents for targeting cancer cells, such as antibodies. Nitroimidazole may be bound to the targeting agent through covalent or non-covalent attachments. For example, nitroimidazoles, such as 2-nitroimidazoles, may be bound to a targeting agent through a linker such as a biodegradable linker. Alternatively, the nitroimidazoles may be bound to a targeting agent through ionic interactions. In certain embodiments, the radiosensitizer of the invention and the additional agent may be enveloped within a liposome.

In certain embodiments, the radiation sensitizer of the invention is associated with a targeting moiety. The targeting moiety may be covalently bound to the nitroimidazole, or associated with the nitroimidazole though non-covalent forces such as ionic bonds, hydrogen bonds, or via encapsulation within a liposome. The targeting moiety, which assists the nitroimidazole in localizing to a particular target region, entering a target tumor cell(s), and/or locating within or proximal to the cell, may be selected on the basis of the particular cell type to be targeted. The targeting moiety may further comprise any of a number of different chemical entities. In one embodiment, the targeting moiety is a small molecule. Molecules which may be suitable for use as targeting moieties in the present invention include haptens, epitopes, and dsDNA fragments and analogs and derivatives thereof. Such moieties bind specifically to antibodies, fragments or analogs thereof, including mimetics (for haptens and epitopes), and zinc finger proteins (for dsDNA fragments). Nutrients believed to trigger receptor-mediated endocytosis and therefore useful targeting moieties include biotin, folate, riboflavin, carnitine, inositol, lipoic acid, niacin, pantothenic acid, thiamin, pyridoxal, ascorbic acid, and the lipid soluble vitamins A, D, E and K. Another exemplary type of small molecule targeting moiety includes steroidal lipids, such as cholesterol, and steroidal hormones, such as estradiol, testosterone, etc.

Targeting moieties may also comprise one or more proteins. Particular types of proteins may be selected based on known characteristics of the target site or target cells. For example, the probe can be an antibody either monoclonal or polyclonal, where a corresponding antigen is displayed at the target site. In situations wherein a certain receptor is expressed by the target cells, the targeting moiety may comprise a protein or peptidomimetic ligand capable of binding to that receptor. Proteins ligands of known cell surface receptors include low density lipoproteins, transferrin, insulin, fibrinolytic enzymes, anti-HER2, platelet binding proteins such as annexins, and biological response modifiers (including interleukin, interferon, erythropoietin and colony-stimulating factor). A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are $F(ab')_2$, Fab', Fab, and $F_v$ fragments, which may be produced by conventional methods or by genetic or protein engineering.

Other preferred targeting moieties include sugars, e.g., glucose, fucose, galactose, mannose, that are recognized by target-specific receptors. For example, instant claimed constructs can be glycosylated with mannose residues, e.g., attached as C-glycosides to a free nitrogen, to yield targeted constructs having higher affinity binding to tumors expressing mannose receptors, e.g., glioblastomas and gangliocytomas, and bacteria, which are also known to express mannose receptors (Bertozzi, C R and M D Bednarski Carbohydrate Research 223:243 (1992); *J. Am. Chem. Soc.* 114:2242, 5543 (1992)), as well as potentially other infectious moieties. Certain cells, such as malignant cells and blood cells (e.g., A, AB, B, etc.) display particular carbohydrates, for which a corresponding lectin may serve as a targeting moiety.

In certain embodiments, chemotherapeutic agents may be administered conjointly with the methods of the invention. Chemotherapeutic agent include those compounds with anti-cancer activity, e.g., compounds that induce apoptosis, compounds that reduce lifespan or compounds that render cells sensitive to stress and include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxanes (paclitaxel, docetaxel), vincristine, vinblastine, nocodazole, epothilones, and navelbine, epipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamine, oxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes (e.g., dacarbazinine (DTIC)); antiproliferative/antimitotic antimetabolites such as folic acid analogs (methotrexate); platinum coordination complexes (cisplatin, carboplatin), procarbazine, hydroxyurca, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; anti secretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; chromatin disruptors.

Radioprotectors may be administered to a patient in combination with the methods described herein. Radioprotectors, also called radioprotectants, are drugs that protect normal (noncancerous) cells from the damage caused by radiation therapy. These agents promote the repair of normal cells that are exposed to radiation. Exemplary radioprotectants include Amifostine (trade name Ethyol®).

In certain embodiments, the methods of the invention further comprise administration of a bacterium such as *salmonella* or genetically engineered variants thereof. Studies have shown that the combination of radiation therapy with *salmonella* increases the effectiveness of tumor suppression particularly in the presence of inflammatory cells called neutrophils. Therapies which combine a nitroimidazoles with a bacterium such as *salmonella* and radiotherapy may enhance tumor suppression.

Radiation sensitizers of the invention may be formulated in a conventional manner using one or more physiologically acceptable carriers or excipients. For example, compounds of the invention and their physiologically acceptable salts and solvates may be formulated for administration by, for example, injection (e.g. subcutaneous, intramuscular, intraparenteral), inhalation or insufflation (either through the mouth or the nose) or oral, buccal, sublingual, transdermal, nasal, parenteral or rectal administration. In one embodiment, a compound of the invention may be administered locally, at the site where the tumor cells are present, i.e., in a specific tissue, organ, or fluid (e.g., blood, cerebrospinal fluid, etc.). Typically, compounds of the invention are administered intravenously.

The phrase "pharmaceutically acceptable" or "physiologically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Radiation sensitizers of the invention can be formulated for a variety of modes of administration. Techniques and formulations generally may be found in Remington's Pharmaceutical Sciences, Meade Publishing Co., Easton, Pa.

In certain embodiments, pharmaceutical compositions may comprise a therapeutically effective amount of a nitroimidazole, for example, at least about 0.1% of a nitroimidazole compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

Toxicity and therapeutic efficacy of compounds of the invention can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Radiation sensitizers of the invention that exhibit large therapeutic indexes are preferred. While radiation sensitizers of the invention that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

A pharmaceutical composition as described herein may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The nitroimidazole, e.g., 2-nitroimidazole, may be formulated into a composition in a free base, neutral or salt form. Pharmaceutically acceptable salts include the salts formed with a free carboxyl group or amine group derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents that delay absorption, such as, for example, aluminum monostearate, gelatin or combinations thereof.

EXAMPLES

Overview

The following example describes an evaluation of the effectiveness of IORT with and without the hypoxic cell radiosensitizer etanidazole for patients with locally advanced primary or locally recurrent colorectal carcinoma (also receiving chemotherapy and external beam irradiation). Results include: (a) percentage and length of local control of disease, (b) disease-free interval and overall survival time in all patients with evaluation of mode and cause of death, and (c) interval to failure and site of failure (local, regional and/or distant).

Patient Selection

All patients meet the following criteria:

(1) Patients are in suitable medical condition to tolerate an operative procedure since an attempt at total or subtotal resection before or after external irradiation is preferred in all patients.

(2) Patients have localized biopsy-proven recurrent (tumor bed or regional nodes) or primary locally advanced carcinoma of the rectum or colon (cecum, ascending, transverse, descending or sigmoid), without evidence of distant metastases (peritoneal or blood borne).

(3) Patients have adequate bone marrow function and peripheral hematologic values with a hemoglobin of more than 10 mg/dl, white blood count of equal to or >40000/mm$^3$ and platelets equal to or >100.000/mm$^3$. They have adequate renal function as evidenced by a BUN of < or equal to 30 mg/dl, or a creatinine of < or equal to 1.5 mg/dl, creatinine clearance of equal to or >50 ml/min., LFT's of <2× normal (bilirubin, SGOT, SGPT, alkaline phosphatase).

(4) If >⅓ of kidney would be within an irradiation field for extrapelvic disease, bilateral renal function is demonstrated on an excretory urogram (IVP), abdominal CT or renal scan.

(5) Patients have a Karnofsky performance status of ≥60%.

(6) Patients receiving prior treatment with 5-FU based adjuvant therapy are eligible for this protocol if the drug was not discontinued because of disease progression.

(7) Orthovoltage and HDR-IORT institutions thickness of residual disease must be ≤1 cm.

Patients are separated into 2 groups.

(1) Group A (no previous EBRT). Patients in Group A receive chemotherapy and standard preoperative irradiation to 45-50.4 Gy. At the time of subsequent exploration and/or resection, or on the day of surgery, the patient is randomized. Treatment is given per the arm assigned. Patients in Group A are randomized between Arm 2-IORT boost of 12.5-20 Gy to tumor bed or unresected tumor alone, or Arm 3-IORT boost of 12.5-20 Gy with etanidazole. Patients undergo surgery/IORT by week 8 following completion of initial chemotherapy and external irradiation. The randomization takes place intraoperatively once it is known of patients are study candidates, but randomization may be carried out earlier on the day of surgery.

(2) Group B (Previous EBERT). Patients in Group B are registered on study and given at least low-dose preop irradiation (20-40 Gy) with continuous infusion 5-FU if safely feasible (Section 6.1.2). On the day of surgery, or preferably the time of exploration/resection, if an IORT boost is feasible, the patient is immediately randomized (Step 2) between Arm 4 intraoperative radiation therapy boost of 15-20 Gy alone or Arm 5-same IORT boost with etanidazole. At the time of surgery and IORT, a maximum resection is carried out, followed by reconstruction.

Radiation Therapy

Patients eligible for the protocol will be treated with preoperative EBRT and chemotherapy combinations and techniques currently recommended by the National Community Cancer Network. If postoperative radiation is required, that will also be applied in accordance with current NCCN recommendations Dose Time Factors and Interval from Operation to External Beam Radiation. In the majority of patients, one should be able to start external beam irradiation within 2-4 weeks of the most recent operation. Suggested intervals by type of operation are as follows: Exploratory only or resection with no bowel or gastric resection-≥2 weeks; Large bowel anastomosis+/−/small bowel-usually 3-4 weeks (occasionally up to 6 weeks); abdominoperineal resection—usually 3-4 weeks (occasionally up to 8 weeks).

External Beam Large Field Component. For Group A, (no prior EBRT), the dose delivered to the extended tumor bed—nodal portal is 45-50.4 Gy/5-6 weeks (1.80 Gy/day, two or more fields per day, 5 days) per week preferably given preoperatively. For Group B (previous EBRT) patients are retreated with a dose of 20-40 Gy preoperatively, 1.8-2 Gy/day (or 1.2 Gy b.i.d) with PV15-FU.

Boost Field. When the extended field is limited to 45 Gy, an additional 5.4 Gy should be delivered, whenever feasible, to a reduced field in 1.8 Gy daily fractions (for a total of 50.4 Gy). Boost fields are treated with multi-field techniques or paired laterals. For pelvic lesions this may include 3-field (PA and laterals), 4-field (lateral and paired posterior obliques, PA-AP and laterals) or non-coplanar techniques. With extrapelvic primaries, treatment in decubitus position with shaped lateral boost portals is often helpful in deleting additional small intestine.

For extra pelvic disease, multiple field techniques may also be feasible for the boost dependent on the location of the disease. If residual involves 1) pancreas: 4-field boost, AP plus laterals, non-coplanar beams; 2) posterior iliac fossa or posterior abdominal wall: PA plus lateral, etc.

Radiation Checklist. During irradiation, patients are seen in status check at least once a week with notation of tolerance, weight and blood counts. Blood counts are obtained at least twice a week until past the nadir and then weekly. If the WBC subsequently falls below 3000 or platelet count below 75,000, twice a week counts should be resumed. If the WBC falls below 2000 or the platelet count below 50,000 during the course of irradiation, treatment should be delayed until the counts rise above these levels.

Treatment port films are obtained for each treatment field and made available for review. Frequency of port films of each field is at least every other week.

RT Treatment Interruptions. Interruptions which are required because of RT-related toxicity or chemotherapy toxicity or major holidays do not result in protocol deviation. Regardless of cause, interruptions which prolong treatment by <10% do not result in protocol variation. Interruptions which prolong treatment by ≥10% constitute a minor protocol variation.

Intraoperative Irradiation, IORT with Electrons (IOERT).

The maximum acceptable tumor thickness (depth) is 5.5 cm. In most instances the lesion is resected before or after the external beam component of irradiation. The area of residual or unresected disease plus a minimum 1-1.5 cm. margin is included within single or abutting intraoperative fields.

IOERT Dose. Doses are specified at the 100% isodose line. The entire tumor is encompassed by the 90% isodose line. Electron energies chosen depends on thickness of tumor bed or unresected tumor (after resection the common energy range is 6-12 MeV and without resection 15-18 MeV), and degree of beam obliquity.

Dose delivered to the 90% isodose depends on amount of remaining disease:

Group A:
1) Resected, recurrent patients only, no residual or microscopic residual—12.5-15 Gy (Given Dose [GD] 13.75-16.5 Gy)
2) Resected, gross residual equal to or less than 2 cm. maximum dimension—15 Gy (GD 16.5 Gy)
3) Unresected or gross residual greater than or equal to 2 cm.—17.5 to 20 Gy (GD 19.25-22 Gy).

Group B:
1) Resected, no residual or microscopic residual—15 to 20 Gy (GD 16.5 to 22 Gy).
2) Unresected or gross residual: 20 Gy (GD 22 Gy).

If a patient has an area of microscopic residual adjacent to gross residual disease, it is desirable to use a shrinking field IOERT technique (i.e., deliver 13.75-16.5 Gy GD to a large field encompassing both gross and microscopic residual; then use reduced cone size or shielding to deliver additional dose to the area of gross residual).

A number of radiation options exist to facilitate accurate delivery of pelvic intraoperative irradiation. These are 1) use of applicators with beveled ends, 2) use of perineal as well as abdominal approaches with prone as well as supine positioning of the patient, 3) increased electron energy if degree of beam obliquity suggests risk of underdosage, 4) use of beam shaping, or when possible, a lower electron energy to decrease volume of a dose limiting organ within the intraoperative field. When possible, uninvolved dose limiting structures which cannot be physically excluded from the treatment field is shielded secondarily with malleable sterilized lead sheets of a thickness appropriate to reduce the dose by 90%.

The maximum acceptable tumor thickness is 1 cm.

Doses are the same as for electron IORT with regard to dose per amount of residual (maximum dimension).

Drug Therapy

Drug therapy will be provided in accordance with current NCCN guidelines for preoperative and adjuvant chemotherapy for locally advanced and recurrent rectal cancer.

Drug Information-Etanidazole (NSC#301467) (NCI IND#21,301). Dosage of etanidazole: the dose of etanidazole to be administered is 12 gm/m$^2$. (This requires in the range of 500 cc of etanidazole in solution.)

Timing of IORT Radiotherapy.

Etanidazole is administered as a running intravenous infusion over a 15 minute period. The surgeon and radiation oncologist determine when it is 45 minutes prior to IORT. Etanidazole infusion begins at that time. Intraoperative radiotherapy is administered no earlier than 20 minutes after the completion of the infusion (equal to or >35 minutes after the start of the infusion). The timing of drug administration starting with time zero as the start of the infusion is recorded. The interval between the completion of drug infusion and IORT is recorded. The duration of drug infusion is also recorded.

The etanidazole solution is infused in a running intravenous solution over a 15 minute period; the duration of drug infusion must be recorded. Blood pressure is carefully monitored during administration, as hypotension may be a side effect.

Surgery

A. Operative Procedures. An adequate procedure is one which allows exploration of the entire abdomen as well as removal of known gross tumor with accompanying mesenteric lymph nodes whenever possible. For rectal lesions a perineal approach alone is not acceptable. Acceptable procedures, therefore, include variants of anterior resection, abdominal-perineal resection or Hartman procedure with end colostomy per the discretion of the operating surgeon. When abdominal-perineal resection is necessary, some form of primary closure of the perineum should be used unless problems with hemostasis exist.

For the purpose of external irradiation following surgery and/or determination of local failure patterns, all margins of tumor or treatment volume are marked with small hemoclips (anterior, superior, inferior and both lateral margins; posterior if applicable). If external irradiation has already been given (Group B), as much gross disease as possible are resected and the full area of recurrent disease marked with hemoclips. Supine and crosstable lateral films are taken and reviewed with the radiation oncologist for the purpose of treatment planning early in the postoperative period. In addition, management of other organs with cancer involvement, i.e., ureter, bladder, uterus and ovary, are handled by standard surgical techniques. This is left to the discretion of the operating surgeon although documentation of the procedure performed must be provided.

B. Operative Procedure With Respect to TORT. The intent of operation is to 1) expose the tumor or tumor bed, 2) resect gross residual if at all possible, and 3) minimize the amount of normal tissue and organs within the intraoperative irradiation field. In most institutions, it should be possible to do the resection and deliver the IORT on the same day, with temporary wound closure during transport of patients from the operating room to radiotherapy when indicated.

At some institutions, a second operation may be necessary for the purpose of delivering IORT. In such instances, major resections may need to be performed in the hospital operating room suites with reoperation in the radiation oncology area within 1-7 days for the IORT.

After adequate exposure and a gross total or subtotal resection of disease is performed, the volume to receive IORT is determined by the surgeon and radiation oncologist and marked with small hemoclips. An intraoperative treatment applicator of appropriate size is chosen and the energy selected. The uninvolved structures which cannot be physically excluded from the treatment field are shielded secondarily with malleable sterilized lead sheet cut-outs of a thickness appropriate to reduce the dose by 90%.

The anesthesia and surgery departments follow their standard transportation policies for transporting the anesthetized patient, if necessary.

Major dose-limiting organs and tissues for IORT include small bowel, large bowel, stomach, spinal cord and nerve. Small bowel and stomach are always be excluded or bypassed and large bowel whenever feasible. Tolerance of large bowel, nerve, vessels, bladder, bone and muscle is evaluated. Potential technical problems include difficulty in obtaining complete tumor bed coverage due to location on a pelvic sidewall, adherence to more than one pelvic location (i.e. sacrum plus lateral pelvic sidewall), narrow pelvis, and inferior location of a lesion making an abdominal approach difficult. The danger of beam obliquity and choice of inadequate electron beam energy is inherent in all of the preceding situations.

The major operative solutions include displacement of all or part of the dose-limiting organs and use of generous incisions to allow maximum flexibility in cone placement both via the abdominal and perineal approaches. Small bowel or suture lines are be included in any IORT boosts but should be totally mobilized. A build up of fluid can occur in the dependent pelvis so constant suction is maintained alongside the cone during treatment.

No anastomosis or diverting procedures are done prior to the TORT if this will bring the suture line into the radiation field. Spillage of urine or bowel contents during the operative procedure is not a contraindication to IORT as these patients all have mechanical bowel prep preoperatively and perioperative antibiotic coverage.

Patients who have received preoperative EBRT of 45-50.40 Gy in 25-28 fractions over 5-5½ weeks are scheduled for re-exploration and resection 3-4 weeks from the date of completion of radiation therapy. The maximum allowable interval is 8 weeks. If the tumor or tumor bed can be included within an IORT field the patient is randomized to receive an IORT boost either with or without etanidazole. If IORT is not feasible, further external irradiation is given, if possible.

For patients with previous EBRT, resection is performed and the intraoperative portion of the irradiation is delivered at that time as above, if possible. External beam irradiation, preferably 20-30 Gy plus PVI 5-FU, precedes surgery/IORT. Post operative irradiation begins 2-4 weeks after surgery when indicated.

In situations where it is inappropriate to operate immediately, e.g., initial re-resection outside parent institution, etc., re-operation for purpose of delivering the intraoperative portion of irradiation can be delayed up to 6 weeks from time of initial resection. If possible, low dose external beam radiation plus CI 5-FU should precede the IORT boost.

INCORPORATION BY REFERENCE

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

What is claimed is:

1. A method of treating cancer in a patient, comprising: (a) administering to a patient with a hypoxic tumor a radiation sensitizer comprising a nitroimidazole; and (b) within one hour after said administration, subjecting the patient to a single dose of 5-20 Gy of stereotactic body radiotherapy.

2. The method of claim 1, wherein the radiation sensitizer comprises a 2-nitroimidazole.

3. The method of claim 2, wherein the radiation sensitizer comprises etanidazole.

4. The method of claim 2, wherein the radiation sensitizer comprises doranidazole.

5. The method of claim 1, wherein the patient is administered the radiation sensitizer and subjected to the stereotactic body radiotherapy within 40 minutes after said administration.

6. The method of claim 1, wherein the cancer is colon cancer, rectal cancer, stomach cancer, lung cancer, cervical cancer, brain cancer, pancreatic cancer, cancer of the head or neck, breast cancer, or cancer of the oral cavity.

7. The method of claim 6, wherein the cancer is of the head or neck.

8. The method of claim 1, wherein the patient is further subjected to a second form of radiation therapy selected from stereotactic body radiotherapy, stereotactic radiosurgery, intensity-modulated radiation therapy, and brachytherapy.

9. The method of claim 8, wherein the second form of radiation therapy is administered one or more days after a resection of a tumor.

10. The method of claim 8, wherein the second form of radiation therapy is administered one or more days before a resection of a tumor.

* * * * *